US012612583B2

(12) United States Patent
Terai et al.

(10) Patent No.: US 12,612,583 B2
(45) Date of Patent: Apr. 28, 2026

(54) DEVICE THAT INTRODUCES SUBSTANCE TO CELLS

(71) Applicant: DAICEL CORPORATION, Osaka (JP)

(72) Inventors: Kazuhiro Terai, Tokyo (JP); Hiroshi Miyazaki, Tokyo (JP); Toru Kitaguchi, Tokyo (JP); Yuko Sakaguchi, Tokyo (JP); Katsuya Miki, Tokyo (JP)

(73) Assignee: Daicel Corporation, Osaka (JP)

( * ) Notice: Subject to any disclaimer, the term of this patent is extended or adjusted under 35 U.S.C. 154(b) by 809 days.

(21) Appl. No.: 17/311,259

(22) PCT Filed: Nov. 29, 2019

(86) PCT No.: PCT/JP2019/046860
§ 371 (c)(1),
(2) Date: Jun. 4, 2021

(87) PCT Pub. No.: WO2020/116353
PCT Pub. Date: Jun. 11, 2020

(65) Prior Publication Data
US 2022/0017847 A1 Jan. 20, 2022

(30) Foreign Application Priority Data
Dec. 7, 2018 (JP) ................................. 2018-230381

(51) Int. Cl.
*C12M 3/06* (2006.01)
*C12M 1/26* (2006.01)
(52) U.S. Cl.
CPC ............ *C12M 23/16* (2013.01); *C12M 33/12* (2013.01)

(58) Field of Classification Search
None
See application file for complete search history.

(56) References Cited

U.S. PATENT DOCUMENTS

| | | | |
|---|---|---|---|
| 11,692,162 B2 * | 7/2023 | Cheng | B01L 3/0293 |
| | | | 422/522 |
| 2013/0237951 A1 * | 9/2013 | Oda | A61M 5/46 |
| | | | 604/500 |

(Continued)

FOREIGN PATENT DOCUMENTS

| | | |
|---|---|---|
| CN | 108472452 A | 8/2018 |
| JP | 2010-252644 A | 11/2010 |
| JP | 2011-067176 A | 4/2011 |

OTHER PUBLICATIONS

Miyazaki et al., "Development of Pyro-Drive Jet Injector With Controllable Jet Pressure", Journal of Pharmaceutical Sciences, 108 (2019), pp. 2415-2420.

(Continued)

*Primary Examiner* — Brian R Gordon
(74) *Attorney, Agent, or Firm* — Knobbe, Martens, Olson & Bear, LLP

(57) ABSTRACT

Proposed is a device that can easily introduce a substance into cells in vitro with high efficiency and in a short time. The device may include an accommodation unit for accommodating a solution containing the cells and the substance. The device may also include a driving unit for pressurization of the solution. Regarding the pressurization of the solution, time from when the pressurization starts until pressure reaches a maximum pressure may be 2.0 msec or shorter.

18 Claims, 1 Drawing Sheet

(56)        References Cited

U.S. PATENT DOCUMENTS

2017/0175139 A1      6/2017  Wu et al.
2018/0304019 A1     10/2018  Oda et al.
2018/0369484 A1 *   12/2018  Nagamatsu ......... A61M 5/3129
2024/0344004 A1 *   10/2024  Malaeb .................. C12M 21/08

OTHER PUBLICATIONS

International Search Report and Written Opinion mailed Feb. 18, 2020 in International Application No. PCT/JP2019/046860, in 15 pages.
Extended European Search Report dated Sep. 2, 2022 in European Application No. 19892828.5.

* cited by examiner

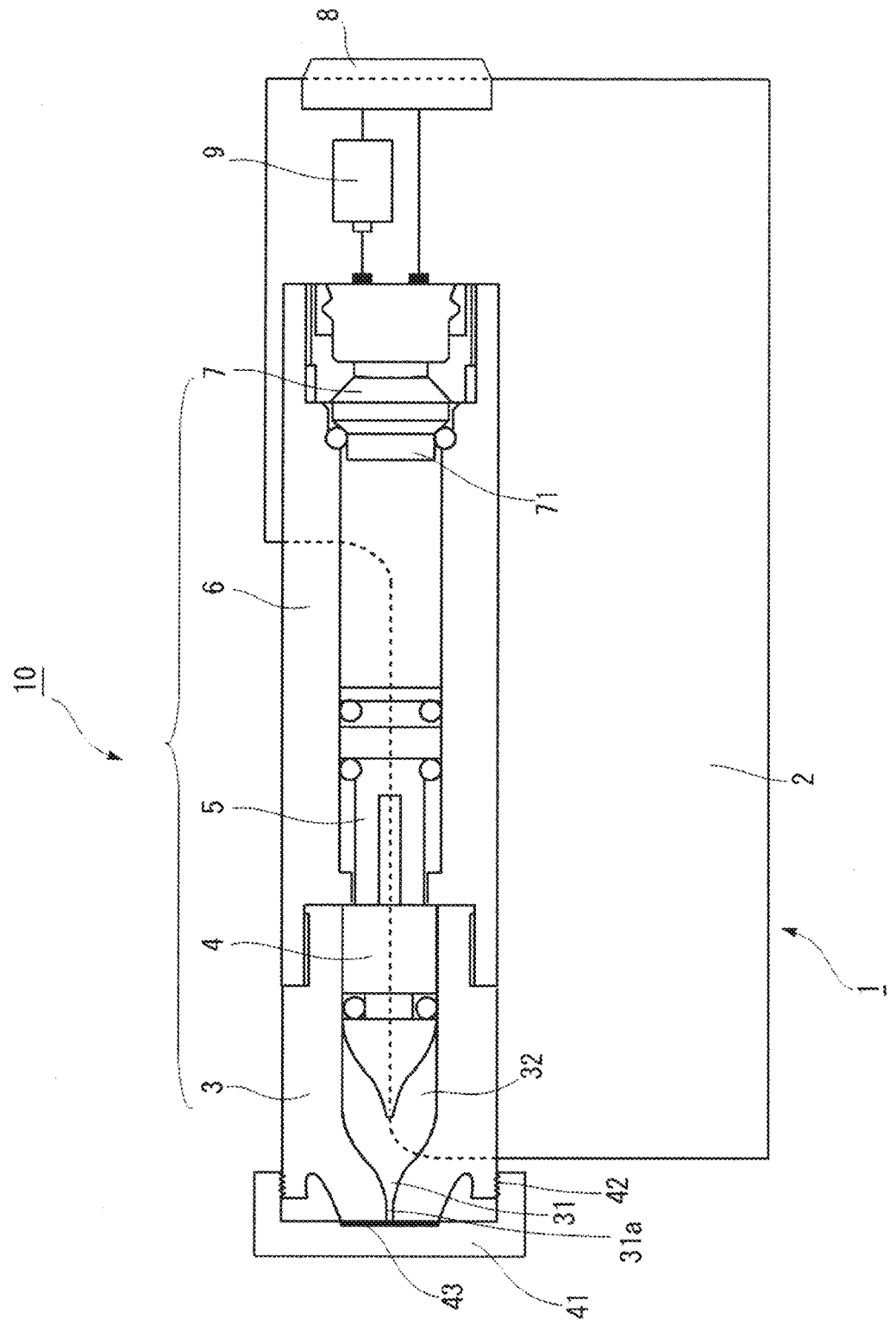

DEVICE THAT INTRODUCES SUBSTANCE TO CELLS

The present application is a U.S. national phase application under 35 U.S.C. § 371 of International Application No. PCT/JP2019/046860, filed on Nov. 29, 2019, which claims the benefit of Japanese Patent Application No. 2018-230381 filed on Dec. 7, 2018, in the Japanese Patent Office, the entire disclosure of each of which is incorporated herein by reference.

TECHNICAL FIELD

The present disclosure relates to a device for introducing a substance into cells in vitro.

BACKGROUND ART

Examples of typical methods of introducing a substance into cells include methods such as microinjection, plasma injection, and laser injection in addition to traditional methods such as electroporation, lipofection, and gene gun.

As a recently developed method, for example, a method using a pressure change is known (Patent Document 1). More specifically, there is a method in which a process of pressurizing animal cells and a process of subsequently depressurizing repeated to introduce a substance into animal cells.

In addition, there is a method in which, while an intracellular introduction substance is present in the vicinity of cells, droplets, which do not contain an intracellular introduction substance and have a predetermined equivalent spherical diameter, are made to collide with cells without using an electrospray, whereby the substance is introduced into animal cells (Patent Document 2).

Although both of the methods are useful, there is a constant demand for a technology that can be easily performed with high efficiency and in a short time as a technology for introducing a substance into cells.

PRIOR ART DOCUMENTS

Patent Document

[Patent Document 1] JP 2011-67176A
[Patent Document 2] JP 2010-252644A

SUMMARY OF THE INVENTION

Problems to be Solved by the Invention

An object of the present disclosure is at least to provide a device that can easily introduce a substance into cells in vitro with high efficiency and in a short time.

Means for Solving the Problems

<1> A device for introducing a substance into cells in vitro, the device comprising:
 an accommodation unit for accommodating a solution containing cells and a substance; and
 a driving unit for pressurization of the solution,
 wherein regarding the pressurization of the solution, time from when the pressurization starts until pressure reaches a maximum pressure is 2.0 msec or shorter.

<2> The device according to <1>, wherein the time from when the pressurization starts until pressure reaches the maximum pressure is 0.05 msec or longer.
<3> The device according to <1> or <2>, wherein the maximum pressure is 0.10 MPa or more.
<4> The device according to any one of <1> to <3>, wherein the maximum pressure is 0.35 MPa or more.
<5> The device according to any one of <1> to <4>, wherein the maximum pressure is 35 MPa or less.
<6> The device according to any one of <1> to <5>, wherein the maximum pressure is 33 MPa or less.
<7> The device according to any one of <1> to <6>, wherein the accommodation unit contains a gas.
<8> The device according to any one of <1> to <7>, wherein the substance is DNA containing a gene.
<9> A method for producing cells into which a substance is introduced in vitro, the method comprising:
 in an accommodation unit for accommodating a solution containing cells and a substance, a step of performing pressurization of the solution,
 wherein regarding the pressurization of the solution, time from when the pressurization starts until pressure reaches a maximum pressure is 2.0 msec or shorter.
<10> The method according to <9>, wherein the time from when the pressurization starts until pressure reaches the maximum pressure is 0.05 msec or longer.
<11> The method according to <9> or <10>, wherein the maximum pressure is 0.10 MPa or more.
<12> The method according to any one of <9> to <11>, wherein the maximum pressure is 0.35 MPa or more.
<13> The method according to any one of <9> to <12>, wherein the maximum pressure is 35 MPa or less.
<14> The method according to any one of <9> to <13>, wherein the maximum pressure is 33 MPa or less.
<15> The method according to any one of <9> to <14>, wherein the accommodation unit contains a gas.
<16> The method according to any one of <9> to <15>, wherein the substance is DNA containing a gene.

Effect of the Invention

According to the present disclosure, at least an effect can be provided in which easily introducing a substance into cells with high efficiency and in a short time can be performed.

BRIEF DESCRIPTION OF THE DRAWINGS

FIG. 1 is a diagram showing a schematic configuration of an injector according to an embodiment.

MODE FOR CARRYING OUT THE INVENTION

An embodiment is a device for introducing a substance into cells in vitro, the device comprising: an accommodation unit for accommodating a solution containing cells and a substance; and a driving unit for pressurization of the solution, wherein regarding the pressurization of the solution, time from when the pressurization starts until pressure reaches a maximum pressure is 2.0 msec or shorter.

Hereinafter, the device will be described as "the device of the present embodiment".

A region of cells into which a substance is introduced may be the cytoplasm or the cell nucleus, but the cell nucleus is preferable. Here, the mode in which a region into which a substance is introduced is the cell nucleus is not a mode in which, according to culturing (for example, culturing for one day or two days) after a substance is introduced into the cytoplasm by the device of the present embodiment, the substance is transferred from the cytoplasm into the cell nucleus but a mode in which a substance is directly introduced into the cell nucleus by an operation of the device of the present embodiment.

In the present embodiment, cells into which a substance is introduced are not particularly limited, and may be prokaryotic cells or eukaryotic cells, and eukaryotic cells are preferable. In addition, animal cells and plant cells may be used, and animal cells are preferable. In addition, adhesive cells and floating cells may be used. In addition, established cells and primary cultured cells may be used.

Animals from which animal cells are derived are not particularly limited, and examples thereof include animals from which cells handled by research institutes are derived. For example, humans, mice, rats, guinea pigs, hamsters (for example, Chinese hamsters), *Drosophila*, and monkeys (for example, African green monkeys) may be exemplified.

The plants from which plant cells are derived are not particularly limited, and examples thereof include seed plants, fern plants, moss plants, and algae. The seed plant may be angiosperm or gymnosperm, and the angiosperm may be monocotyledon or dicotyledon.

The substance in the present embodiment is not particularly limited, and examples thereof include biomolecules. The biomolecules are not particularly limited as long as they function in cells when they are introduced into the cells. In addition, the biomolecules may be a natural product or artificially synthesized product. Examples thereof include nucleic acids or derivatives thereof; nucleosides, nucleotides or derivatives thereof; amino acids, peptides, proteins or derivatives thereof; lipids or derivatives thereof; sugars or derivatives thereof; metal ions; low-molecular-weight compounds or derivatives thereof; antibiotics; and vitamins or derivatives thereof. The nucleic acid may be DNA or RNA. The DNA may be DNA including a gene. When the substance is DNA including a gene, since an introduction target is the cytoplasm and/or the cell nucleus of the cells, the gene is expected to be expressed by culturing the cells into which the gene is introduced.

The form of the substances and a solvent are not particularly limited as long as substances are stably present and there is no adverse effect such as destruction of cells themselves and functions of the cells, into which substances are introduced and may be a free form, a form in which substances are fixed to carriers such as nanoparticles, a modified form.

When the substance is DNA including a gene, DNA may have a design form in which the gene is contained in an expression cassette or expression vector. In addition, for example, the gene may be provided under control of a promoter suitable for the type of the cells into which DNA is introduced.

That is, for example, when the substances are biomolecules, in any of the forms, the biomolecules can be prepared by using a known genetic engineering technique.

Examples of a method of analyzing a proportion of a substance introduced into cells include known methods in which molecules that emit fluorescence are directly used as a substance of the present embodiment or analysis is performed using a substance labeled with fluorescent molecules and using a fluorescence intensity as an index.

Regarding pressurization of a solution containing cells and a substance, the time from when pressurization starts until the pressure reaches a maximum pressure is 2.0 msec or shorter.

Here, the pressure is the pressure in the accommodation unit. The measurement method is not particularly limited, and for example, when the pressure is measured using an injector described in examples to be described below, it can be measured using a method described in the column of "method of measuring the pressure in the accommodation unit" to be described below.

The time from when pressurization starts until the pressure reaches the maximum pressure is preferably 2.0 msec or shorter, more preferably 1.0 msec or shorter, and still more preferably 0.5 msec or shorter. When the time is within the above range, it is expected that a substance would be able to be efficiently introduced into cells. In addition, the lower limit thereof is not particularly limited, but is generally longer than 0, for example, 0.05 msec or longer.

In addition, the maximum pressure is preferably 0.10 MPa or more, more preferably 0.20 MPa or more, and still more preferably 0.35 MPa or more. When the maximum pressure is 0.10 MPa or more, it is expected that cells would be deformed when a substance is introduced into the cells and the substance would be efficiently introduced.

In addition, the maximum pressure is preferably 35 MPa or less, more preferably 34 MPa or less, and still more preferably 33 MPa or less. When the maximum pressure exceeds 35 MPa, the cells may be killed. When the maximum pressure is 35 MPa or less, it is expected that a substance would be able to be introduced into cells without killing the cells.

In a preferable aspect of the present embodiment, in the device of the present embodiment, the accommodation unit contains a gas because in this case the efficiency of introducing a substance into cells increases. Regarding the gas, air may be exemplified. In addition, nitrogen, oxygen, ozone, carbon dioxide, hydrogen, and carbon monoxide may be exemplified, and a mixed gas of any two or more thereof may be exemplified.

In addition, preferably, the gas is a gas that does not contain microorganisms or the like.

The air may be generally used air, and its composition is not particularly limited. For example, a mixed gas containing about 80% of nitrogen and about 20% of oxygen may be exemplified.

In the present embodiment, the ratio of the volume of the gas to the volume of the accommodation unit is not particularly limited as long as introduction of a substance into cells is not inhibited, and is preferably 10% or more, more preferably 20% or more, still more preferably 30% or more, still more preferably 40% or more, still more preferably 50% or more, still more preferably 60% or more, still more preferably 70% or more, still more preferably 80% or more, and still more preferably 90% or more. On the other hand, the upper limit is, for example, 95% or less.

The structure and material of the accommodation unit in which a solution containing cells and a substance is accommodated are not particularly limited as long as they can withstand pressurization. In a preferable aspect, the same applies when the accommodation unit further contains a gas.

The structure and material of the driving unit are not particularly limited. The pressurization may be caused by, for example, a pressure generated when the pressure of the compressed gas is released, or a pressure generated by combustion of an explosive that is ignited by an ignition device. In addition, pressurization using electrical energy of a piezoelectric element or the like or mechanical energy of a spring or the like as pressurization energy may be performed, and pressurization using pressurization energy generated by appropriately combining these forms of energy may be performed.

When a form in which a pressure generated by combustion of an explosive that is ignited by an ignition device is used for pressurization is used, the explosive may be, for example, any explosive among an explosive containing zirconium and potassium perchlorate (ZPP), an explosive containing titanium hydride and potassium perchlorate (THPP), an explosive containing titanium and potassium perchlorate (TiPP), an explosive containing aluminum and potassium perchlorate (APP), an explosive containing aluminum and bismuth oxide (ABO), an explosive containing aluminum and molybdenum oxide (AMO), an explosive containing aluminum and copper oxide (ACO), and an explosive containing aluminum and iron oxide (AFO) or an explosive composed of a plurality of combinations of these. Regarding a feature of these explosives, if the combustion products are gases in a high temperature state, since they do not contain gas components at room temperature, the combustion products after ignition immediately condense.

Examples of the device of the present embodiment include an injector. Hereinafter, details thereof will be described.

In the injector as an example of the device of the present embodiment, a solution containing cells and a substance is not accommodated in the accommodation unit from the beginning, and the solution is accommodated in the accommodation unit by sucking through a nozzle having an injection port. In this manner, when a configuration in which a filling operation in the accommodation unit is required is used, it is possible to accommodate a solution containing desired cells and a desired substance. Therefore, in the injector, a syringe part is removable. Here, when the gas is accommodated in the accommodation unit, a gas may be sucked for accommodation after the solution is accommodated or a gas may be sucked first for accommodation and the solution may then be accommodated. In addition, the injection port of the nozzle tip is sealed so that a solution containing cells and a substance is prevented from being injected. A sealing member and a sealing method are not particularly limited as long as a solution containing cells and a substance is prevented from being injected. In a mode in which the accommodation unit contains a gas, sealing is performed so that a solution containing cells and a substance and also a gas are prevented from being injected. A sealing member and a sealing method are not particularly limited as long as a solution containing cells and a substance is prevented from being injected.

Hereinafter, regarding an example of an injector, a syringe 1 (needleless syringe) will be described with reference to the drawings. Note that each of the configurations, combinations thereof, and the like in the embodiments are an example, and various additions, omissions, substitutions, and other changes may be made as appropriate without departing from the spirit of the present invention. The present invention is not limited by the embodiments and is limited only by the claims. The same applies to examples to be described below. Here, the terms "distal end side" and "proximal end side" are used as terms that represent the relative positional relationships in the syringe 1 in the longitudinal direction. The "distal end side" represents a position near the tip of the syringe 1 to be described below, that is, near an injection port 31a, and the "proximal end side" represents a side on the side opposite to the "distal end side" of the syringe 1 in the longitudinal direction, that is, a side on the side of a driving unit 7. In addition, this example is an example in which combustion energy of an explosive that is ignited by an ignition device is used and an accommodation unit for accommodating a solution containing cells and a substance is pressurized, but the present embodiment is not limited thereto.

(Configuration of Syringe 1)

FIG. 1 is a diagram showing a schematic configuration of the syringe 1 and is a cross-sectional view of the syringe 1 in the longitudinal direction. The syringe 1 has a configuration in which a syringe assembly 10 in which a sub-assembly including a syringe part 3 and a plunger 4 and a sub-assembly including a syringe main body 6, a piston 5, and the driving unit 7 are integrally assembled is mounted in a housing (syringe housing) 2.

As described above, the syringe assembly 10 is configured to be detachable from the housing 2. An accommodation unit 32 formed between the syringe part 3 and the plunger 4 included in the syringe assembly 10 is filled with a solution containing cells and a substance, and the syringe assembly 10 is a unit that is discarded whenever the substance is introduced into the cells. As shown in FIG. 1, the accommodation unit 32 includes a nozzle 31 and an injection port 31a. On the other hand, on the side of the housing 2, a battery 9 that supplies power to an igniter 71 included in the driving unit 7 of the syringe assembly 10 is included. When a user performs an operation of pressing a button 8 provided in the housing 2, supply of power from the battery 9 is performed between an electrode on the side of the housing 2 and an electrode on the side of the driving unit 7 of the syringe assembly 10 via a wiring. Here, the shape and position of both electrodes are designed so that the electrode on the side of the housing 2 and the electrode on the side of the driving unit 7 of the syringe assembly 10 are automatically brought in contact when the syringe assembly 10 is mounted in the housing 2. In addition, the housing 2 is a unit that can be repeatedly used as long as power that can be supplied to the driving unit 7 remains in the battery 9. Here, in the housing 2, when the battery 9 has no power, only the battery 9 may be replaced, and the housing 2 may be continuously used. In addition, the injection port 31a at the tip of the nozzle 31 is sealed with a sealing part 43 so that a solution containing the cells and the substance is prevented from being injected. The sealing part 43 is fixed to a cap 41. In addition, the cap 41 is fixed to the syringe part 3 via a fixing part 42.

An another embodiment is a method for producing cells into which a substance is introduced in vitro, the method comprising: in an accommodation unit for accommodating a solution containing cells and a substance, a step of performing pressurization of the solution, wherein regarding the pressurization of the solution, time from when the pressurization starts until pressure reaches a maximum pressure is 2.0 msec or shorter.

The details refer to description of the device for introducing a substance into cells in vitro as described above.

EXAMPLES

Examples will be described below, but none of the examples should be interpreted with a limited meaning.

In the following examples, first, examples in which the ratio of the volume of the gas to the volume of the accommodation unit is 0 will be described, and then examples in which the accommodation unit contains a gas will be described.

[Method of Measuring Pressure in Accommodation Unit]

In the following examples, the injector shown in FIG. 1 was used as a device for introducing a substance into cells and the substance was introduced into the cells in the accommodation unit of the injector. The time from when pressurization started until the pressure reached a maximum pressure and the maximum pressure were measured as follows.

The accommodation unit was filled with 100 μl of distilled water (the ratio of the volume of the gas to the volume of the accommodation unit was 0), and mounted on the injector. The nozzle tip of the accommodation unit and a piezoelectric element (M60-1L-M3 commercially available from Muller) were connected via a jig made of a Teflon (registered trademark) resin. A piezoelectric element signal was acquired by a digital oscilloscope TBS2102 (commercially available from Tektronics). The timing of data acquisition by the digital oscilloscope was controlled according to a trigger signal from a device power supply. From the initial operation time of the device and the time showing the maximum peak, the time from when pressurization started until the pressure reached the maximum pressure was calculated. In addition, since the maximum pressure was digitally output as a numerical value, the maximum value thereof was used. Here, the pressure obtained by the measurement method was the same as the pressure in the accommodation unit, and the pressure obtained by the measurement method could be used as the pressure in the accommodation unit.

The results are shown in Table 1. Here, each measurement was independently performed two to three times. Table 1 shows an average value of the times from when pressurization started until the pressure reached the maximum pressure and the minimum value (*1) and the maximum value (*2) of the maximum pressure.

TABLE 1

| Amount of ZPP | Time from when pressurization starts until pressure reaches maximum pressure (msec) | Maximum pressure (MPa) |
|---|---|---|
| 15 mg | 0.063 | (*1) 0.350 |
| | | (*2) 0.470 |
| 45 mg | 0.091 | (*1) 9.380 |
| | | (*2) 14.06 |
| 75 mg | 0.129 | (*1) 17.58 |
| | | (*2) 19.53 |
| 110 mg | 0.135 | (*1) 29.30 |
| | | (*2) 32.03 |

[Example 1] Introduction of Plasmid DNA into Cell Nuclei of Established Cells (Adhesive Cells)

Human fetal kidney cells 293 (HEK293 cells) were subcultured until the day before the test, and specifically, subcultured at 37° C. and with 5% carbon dioxide in a Dulbecco's Modified Eagle's Medium (DMEM) (Nacalai Tesque) containing 10% fetal bovine serum and penicillin-streptomycin. Cells were collected using TrypLE Express (GIBCO), and adjustment was performed in a Dulbecco's Modified Eagle's Medium (DMEM) so that the concentration was $5 \times 10^5$ cells/100 μl.

1.25 μg of a Cy3-labeled plasmid DNA solution (Mirus) was added to 100 μl of a cell suspension which was mixed well to prepare a solution containing HEK293 cells and Cy3-labeled plasmid DNA. 100 μl of the solution was sucked up from a nozzle of an injector into the accommodation unit of the injector (the ratio of the volume of the gas to the volume of the accommodation unit was 0). Here, the injector was used as a device for introducing Cy3-labeled plasmid DNA into cells, and is the injector shown in FIG. 1. In this example, a condition of 110 mg of ZPP was set for the injector, and on the side of the nozzle of the accommodation unit, the cap was firmly mounted, and thus an ignition operation was performed while the inside of the accommodation unit was sealed. Thereby, the solution containing Cy3-labeled plasmid DNA was introduced into HEK293 cells. Under these conditions, regarding the pressurization of the solution containing HEK293 cells and Cy3-labeled plasmid DNA, the time from when the pressurization started until the pressure reached the maximum pressure was 0.135 msec, and the maximum pressure was (*1) 29.30 MPa and (*2) 32.03 MPa.

Then, the accommodation unit was removed from the injector, and the content was collected by pushing it out of the nozzle into a 1.5 ml tube. Cells were made into pellets by centrifugation at 1,200×g for three minutes, and a slide was prepared using a DAPI-containing encapsulant (Invitrogene). Observation under a fluorescence microscope (Keyence) was performed, and the number of nuclei of DAPI-stained cells and the number of nuclei of cells in which DAPI and Cy3 were merged were visually counted to calculate the rate of introduction of Cy3 into cell nuclei.

Example 2, Example 3, and Example 4

The conditions were the same as in Example 1 except that the amount of explosive was changed as shown in Table 2. The results are shown in Table 2 together with the results of Example 1.

Based on this fact, it was confirmed that Cy3-labeled plasmid DNA could be introduced into cell nuclei of HEK293 cells (adhesive cells) using the injector as the device of the present embodiment. In addition, therefore, those skilled in the art can understand that, when DNA containing genes is used as a substance, the genes can be expressed by culturing cells into which the genes are introduced.

TABLE 2

| | Amount of ZPP | Rate of introduction of Cy3 into cell nuclei |
|---|---|---|
| Example 1 | 110 mg | 8.85% |
| Example 2 | 75 mg | 5.79% |
| Example 3 | 45 mg | 5.97% |
| Example 4 | 15 mg | 5.84% |

[Example 5] Introduction of Dextran into Established Cells (Adhesive Cells)

HEK293 cells were subcultured in the same manner as in Example 1, and the cells were collected. The cells were adjusted in a Dulbecco's Modified Eagle's Medium (DMEM) so that an appropriate cell concentration (5 to $10 \times 10^5$ cells/30 μl) was obtained.

5 μl of fluorescein isothiocyanate-dextran (FITC-Dextran) (4.5 kDa) (SIGMA aldrich) dissolved in 20 μg/μl with PBS, that is, 100 μg, was added to 30 μl of a cell suspension which was mixed well to prepare a solution containing HEK293 cells and FITC-Dextran. 30 μl of the solution was sucked up from a nozzle of an injector into the accommodation unit of the injector (the ratio of the volume of the gas to the volume of the accommodation unit was 0). Here, the injector was used as a device for introducing FITC-Dextran into cells, and is the injector shown in FIG. 1 as in Example 1. In this example, a condition of 45 mg of ZPP was set for the injector, and on the side of the nozzle of the accommodation unit, the cap was firmly mounted, and thus an ignition operation was performed while the inside of the accommodation unit was sealed. Thereby, the solution containing FITC-Dextran was introduced into HEK293 cells. Under these conditions, regarding the pressurization of the solution containing HEK293 cells and FITC-Dextran, the time from when the pressurization started until the pressure reached the maximum pressure was 0.091 msec, and the maximum pressure was (*1) 9.380 MPa and (*2) 14.06 MPa.

Then, the accommodation unit was removed from the injector, and the content was collected by pushing it out of the nozzle into a 1.5 ml microtube.

Then, 500 µl of PBS was added and mixed well, and centrifuged at 1,200×g for three minutes. This was repeated twice to wash the cells.

The pellets were suspended in 500 µl of Triton X-100 (Nacalai Tesque) (w/v) (0.2% Triton X-100 solution) prepared at 0.2% with PBS and mixed well with a Vortex (Scientific Industries) for 15 seconds. Then, the sample was left at room temperature for 10 minutes, and the cell membrane was destroyed. Centrifugation was performed at 22,400×g for 15 minutes, 150 µl of the supernatant was separated out and put into one well of a MICRO WELL PLATE (As One Corporation). In addition, 150 µl was separated out and put into another well.

The fluorescence intensity was measured as follows. That is, the fluorescence of FITC was measured with a corona multigrating microplate reader (HITACHI) using a filter having an absorption wavelength of 480 nm, and a fluorescence wavelength of 520 nm.

Here, a 0.2% Triton X-100 solution was used for the blank.

Comparative Example 5

This example was the same as Example 5 except that the ignition operation by the injector was not performed.

The fluorescence intensity (a.u.) of Comparative Example 5 was 76, but the fluorescence intensity (a.u.) of Example 5 was 321.5. Based on this fact, it was confirmed that FITC-Dextran could be introduced into established cells (adhesive cells) using the injector as the device of the present embodiment.

Example 6 and Example 7

The conditions were the same as in Example 5 except that the amount of explosive was changed as shown in Table 3. The results are shown in Table 3 together with the results of Example 5.

Example 8

This example was the same as Example 5 except for the following. That is, adjustment in a Dulbecco's Modified Eagle's Medium (DMEM) was performed so that the cell concentration was $10 \times 10^5$ cells/100 µl. 5 µl of fluorescein isothiocyanate-dextran (FITC-Dextran) (4.5 kDa) (SIGMA aldrich) dissolved in 20 µg/µl with PBS, that is, 100 µg, was added to 100 µl of a cell suspension which was mixed well to prepare a solution containing HEK293 cells and FITC-Dextran. 100 µl of the solution was sucked up from a nozzle of an injector into the accommodation unit of the injector (the ratio of the volume of the gas to the volume of the accommodation unit was 0). In addition, the amount of explosive was changed to 15 mg. Under these conditions, regarding the pressurization of the solution containing HEK293 cells and FITC-Dextran, the time from when the pressurization started until the pressure reached the maximum pressure was 0.063 msec, and the maximum pressure was (*1) 0.350 MPa and (*2) 0.470 MPa.

Comparative Examples 6 to 8

These examples were the same as Examples 6 to 8 respectively, except that the ignition operation by the injector was not performed.

The results are shown in Table 3. Based on this fact, it was confirmed that FITC-Dextran could be introduced into established cells (adhesive cells) using the injector as the device of the present embodiment.

TABLE 3

| Amount of ZPP | Example | | Comparative Example | |
|---|---|---|---|---|
| | Example No. | Fluorescence intensity (a.u.) | Comparative Example No. | Fluorescence Intensity (a.u.) |
| 45 mg | Example 5 | 321.5 | Comparative Example 5 | 76 |
| 110 mg | Example 6 | 249.5 | Comparative Example 6 | 124 |
| 75 mg | Example 7 | 320.5 | Comparative Example 7 | 76.5 |
| 15 mg | Example 8 | 305.5 | Comparative Example 8 | 40.5 |

[Reference Example 5-1] Introduction of Dextran into Established Cells (Adhesive Cells) with Destroyed Cell Membrane HEK293 cells were subcultured in the same method as in Example 1, and the cells were collected. Adjustment in a Dulbecco's Modified Eagle's Medium (DMEM) was performed so that the concentration was $10 \times 10^5$ cells/30 µl.

In this reference example, unlike Example 5, before the operation using the injector, pores were formed in the cell membrane, which was an intracellular and extracellular partition wall, using Triton X-100, and even if FITC-Dextran was introduced into cells, a situation in which it did not remain in the cells was created. If the fluorescence intensity of this reference example was significantly smaller than the fluorescence intensity obtained in Example 5, the fact that introduction of the substance had been performed by an operation using the injector was shown from an aspect different from the results of Example 5 and Comparative Example 5.

30 µl of the cell suspension was sucked up from a nozzle of an injector into the accommodation unit of the injector (the ratio of the volume of the gas to the volume of the accommodation unit was 0). The injector was the injector shown in FIG. 1 as in Example 1. In addition, 3 µl of 2% Triton X-100 was sucked up and left for about five minutes, and then 5 µl of fluorescein isothiocyanate-dextran (FITC-Dextran) (4.5 kDa) (SIGMA aldrich) dissolved in 20 µg/µl with PBS, that is, 100 µg, was added and mixed well.

In this example, a condition of 75 mg of ZPP was set for the injector, and on the side of the nozzle of the accommodation unit, the cap was firmly mounted, and thus an ignition operation was performed while the inside of the accommodation unit was sealed. Under these conditions, regarding the pressurization of the solution containing HEK293 cells and FITC-Dextran, the time from when the pressurization started until the pressure reached the maximum pressure was 0.129 msec, and the maximum pressure was (*1) 17.58 MPa and (*2) 19.53 MPa.

Then, the accommodation unit was removed from the injector, and the content was collected by pushing it out of the nozzle into a 1.5 ml microtube.

Then, the cells were washed as in Example 5, and the fluorescence intensity was measured.

Reference Example 5-2

This example was the same as Reference Example 5-1 except that the ignition operation by the injector was not performed.

Reference Example 5-3

This example was a test example in which an ignition operation was performed using the injector without destroying the cell membrane with Triton X-100 and was substantially the same test example as Example 7.

Reference Example 5-4

This example was a test example in which the cell membrane was not destroyed with Triton X-100, and an ignition operation using the injector was not performed and was substantially the same test example as Comparative Example 7.

The results are shown in Table 4. Based on this fact, it was confirmed that FITC-Dextran could be introduced into established cells (adhesive cells) using the injector as the device of the present embodiment.

In addition, it was confirmed that, in Reference Example 5-2 and Reference Example 5-4, regardless of treatment with Triton X-100, there was no significant difference in the fluorescence intensity. On the other hand, it was confirmed that, based on the results of Reference Example 5-1, even if the ignition operation was performed, when pores were formed in the cell membrane which was an intracellular and extracellular partition wall, using Triton X-100, the fluorescence intensity was significantly smaller than that of Reference Example 5-3 as in Reference Example 5-2 and Reference Example 5-4.

TABLE 4

| | Treatment with Triton X-100 | Ignition operation | Fluorescence intensity (a.u.) |
|---|---|---|---|
| Reference Example 5-1 | YES | YES | 99.5 |
| Reference Example 5-2 | YES | NO | 167.5 |
| Reference Example 5-3 | NO | YES | 935 |
| Reference Example 5-4 | NO | NO | 162 |

[Example 9] Introduction of Dextran into Primary Cells (Floating Cells)

Spleen tissues were collected from living mice (BALB/c, 8-week old, female, CLEA Japan, Inc.) by a general method and washed twice with PBS. In addition, the tissues were transferred to PBS in a 10 cm dish (FALCON) and cells were collected from the tissues using UV sterilized tweezers. An entire amount of the cell suspension was transferred into a 15 ml conical tube (FALCON) and left for two minutes, and the supernatant was transferred into another 15 ml conical tube (FALCON). Centrifugation was performed at 1,000×g for five minutes, pellets were resuspended in 10 ml of PBS, and the same centrifugation was performed. The pellets were resuspended in 1 ml of PBS, the number of cells was measured, and adjustment with PBS was performed so that an appropriate cell concentration ($10 \times 10^5$ cells/100 µl) was obtained.

Then, the same method as in Example 5 was performed except that the condition of 75 mg of ZPP was set. Therefore, under these conditions, regarding the pressurization of the solution containing mouse spleen cells and FITC-Dextran, the time from when the pressurization started until the pressure reached the maximum pressure was 0.129 msec, and the maximum pressure was (*1) 17.58 MPa and (*2) 19.53 MPa.

Comparative Example 9

This example was the same as Example 9 except that the ignition operation by the injector was not performed.

As a result, the fluorescence intensity (a.u.) of Comparative Example 9 was 67.5, but the fluorescence intensity (a.u.) of Example 9 was 317.5.

Based on this fact, it was confirmed that FITC-Dextran could be introduced into primary cells (floating cells) using the injector as the device of the present embodiment.

Hereinafter, examples in which the accommodation unit contains a gas will be described.

[Example 10] Introduction of Plasmid DNA into Established Cells (Adhesive Cells)

HEK293 cells were collected in the same manner as in Example 1, and 100 µl, 70 µl, 50 µl, 30 µl or 10 µl of cell suspensions containing $5.5 \times 10^5$ cells were prepared. A DMEM containing 2.5 µg of Cy3-labeled plasmid DNA was used for cell suspension. The solution was sucked up from a nozzle of an injector into the accommodation unit of the injector. When the ratio of the volume of the gas to the volume of the accommodation unit was 0%, the entire amount of the cell suspension was sucked up. On the other hand, except when the ratio of the volume of the gas to the volume of the accommodation unit was 0%, after sucking up the cell suspension by that volume, the plunger was pulled up to a gradation of 100 µl so that air in the general laboratory was filled in. That is, the ratio of the volume of the gas to the volume of the accommodation unit was 0%, 30%, 50%, 70%, and 90%, respectively. Here, the injector was used as a device for introducing Cy3-labeled plasmid DNA into cells, and was the injector shown in FIG. 1. In this example, a condition of 75 mg of ZPP was set for the injector, and on the side of the nozzle of the accommodation unit, the cap was firmly mounted, and thus an ignition operation was performed while the inside of the accommodation unit was sealed. Thereby, the solution containing Cy3-labeled plasmid DNA was introduced into HEK293 cells.

Then, the accommodation unit was removed from the injector, and the content was collected by pushing it out of the nozzle into a 1.5 ml microtube.

Then, 500 μl of PBS (phosphate-buffered saline, Nacalai Tesque) was added and mixed well, and centrifuged at 1,200×g for three minutes. This was repeated twice to wash the cells.

Pellets were resuspended in 200 μl of PBS, and mixed well by pipetting. Then, single cells were screened with a round tube with cell-strainer cap (FALCON), the cells were separated using a filter that detects Cy3 fluorescence with a flow cytometer BD FACS CantII (commercially available from BD), and the intracellular introduction rate of Cy3-labeled plasmid DNA was calculated.

Comparative Example 10

This example was the same as Example 10 except that the ignition operation by the injector was not performed.

The results are shown in Table 5. Based on this fact, it was confirmed that, when the accommodation unit contained air, and moreover, as the ratio of the volume of air to the volume of the accommodation unit increased, Cy3-labeled plasmid DNA could be introduced into HEK293 cells (adhesive established cells) with high efficiency.

TABLE 5

| | Amount of ZPP | Ratio of volume of air to volume of accommodation unit | Rate of introduction of Cy3 into cells |
|---|---|---|---|
| Example 10 | 75 mg | 0% | 3.0% |
| | | 30% | 6.4% |
| | | 50% | 4.7% |
| | | 70% | 15.1% |
| | | 90% | 23.9% |
| Comparative Example 10 | NO | 0% | 2.4% |

[Example 11] Introduction of Dextran into Established Cells (Adhesive Cells)

This example was the same as Example 10 except that a DMEM containing 100 μg of fluorescein isothiocyanate-dextran (FITC-Dextran) (4.5 kDa) was used for cell suspension. In addition, the cells were separated using a filter that detects FITC fluorescence with a flow cytometer, and the rate of introduction of FITC-Dextran (4.5 kDa) into cells was calculated.

Comparative Example 11

This example was the same as Example 11 except that the ignition operation by the injector was not performed.

Example 12

The conditions were the same as in Example 11 except that the amount of explosive was changed to 45 mg.

Comparative Example 12

This example was the same as Example 12 except that the ignition operation by the injector was not performed and was substantially the same test example as Comparative Example 11.

The results are shown in Table 6. Based on this fact, it was confirmed that, when the accommodation unit contained air, and moreover, the ratio of the volume of air to the volume of the accommodation unit increased, FITC-Dextran could be introduced into HEK293 cells (adhesive established cells) with high efficiency.

TABLE 6

| | Amount of ZPP | Ratio of volume of air to volume of accommodation unit | Rate of introduction of FITC-Dextran into cells |
|---|---|---|---|
| Example 11 | 75 mg | 0% | 43.9% |
| | | 30% | 59.4% |
| | | 50% | 70.4% |
| | | 70% | 68.2% |
| | | 90% | 91.9% |
| Comparative Example 11 | NO | 0% | 9.8% |
| Example 12 | 45 mg | 0% | 25.0% |
| | | 30% | 36.1% |
| | | 50% | 41.8% |
| | | 70% | 49.6% |
| | | 90% | 85.1% |
| Comparative Example 12 | NO | 0% | 6.0% |

DESCRIPTION OF REFERENCE NUMERALS

1: Syringe, 2: Housing, 3: Syringe part, 4: Plunger, 5: Piston, 6: Syringe main body, 7: Driving unit, 8: Button, 9: Battery, 10: Syringe assembly, 31: Nozzle, 31*a*: Injection port, 32: Accommodation unit, 41: Cap, 42: Fixing part, 43: Sealing part, 71: Igniter

The invention claimed is:

1. A device for introducing a substance into cells in vitro, the device comprising:

a housing; a syringe assembly detachably coupled to the housing, the syringe assembly comprising a syringe part, a plunger, a piston, an igniter, and a driving unit operatively coupled to each other, the syringe part coupled to the plunger, the plunger coupled to the piston, the piston coupled to the driving unit, and the igniter included in the driving unit;

a button provided in the housing;

a power source provided in the housing and coupled to the button, the power source configured to provide power to the igniter in response to the button being activated;

an accommodation unit disposed between and coupled to the syringe part and the plunger and accommodating a solution containing the cells and the substance, the accommodation unit comprising:

a nozzle, and an injection port disposed at a tip of the nozzle;

the piston coupled with the accommodation unit via the plunger;

the driving unit operatively coupled with the piston and the plunger, the driving unit causing a pressure in the accommodation unit to reach a maximum pressure in not longer than 2.0 msec from a pressurization start time for the solution by controlling the piston and the plunger to pressurize the solution accommodated in the accommodation unit through movement of the piston and the plunger;

a sealing part sealing the injection port to prevent the solution from being injected from the accommodation unit to an outside of the syringe assembly via the injection port at least until the pressure in the accommodation unit reaches the maximum pressure; and a cap covering both the sealing part and a front portion of the syringe part that is aligned with the injection port of the nozzle, the cap fixing the sealing part to the front portion of the syringe part such that the sealing part is positioned between, and in contact with, the injection port and an inner surface of the cap.

2. The device according to claim 1, wherein the driving unit causes the pressure in the accommodation unit to reach the maximum pressure in not shorter than 0.05 msec and not longer than 2 msec from the pressurization start time by controlling the piston and the plunger to pressurize the solution accommodated in the accommodation unit.

3. The device according to claim 1, wherein the driving unit causes a pressure in the accommodation unit to reach the maximum pressure of 0.10 MPa or more by controlling the piston and the plunger to pressurize the solution accommodated in the accommodation unit.

4. The device according to claim 1, wherein the driving unit causes a pressure in the accommodation unit to reach the maximum pressure of 0.35 MPa or more by controlling the piston and the plunger to pressurize the solution accommodated in the accommodation unit.

5. The device according to claim 1, wherein the driving unit causes a pressure in the accommodation unit to reach the maximum pressure of 35 MPa or less by controlling the piston and the plunger to pressurize the solution accommodated in the accommodation unit.

6. The device according to claim 1, wherein the driving unit causes a pressure in the accommodation unit to reach the maximum pressure of 33 MPa or less by controlling the piston and the plunger to pressurize the solution accommodated in the accommodation unit.

7. The device according to claim 1, wherein the accommodation unit additionally contains a gas.

8. The device according to claim 1, wherein the substance is DNA containing a gene.

9. The device according to claim 1, wherein the driving unit causes the pressure in the accommodation unit to reach the maximum pressure in not longer than 1 msec from the pressurization start time by controlling the piston and the plunger to pressurize the solution accommodated in the accommodation unit.

10. The device according to claim 1, wherein the driving unit causes the pressure in the accommodation unit to reach the maximum pressure in not longer than 0.5 msec from the pressurization start time by controlling the piston and the plunger to pressurize the solution accommodated in the accommodation unit.

11. A method for introducing a substance into cells *in vitro*, the method comprising:
    providing a housing and a syringe assembly detachably coupled to the housing, the syringe assembly comprising a syringe part, a plunger, a piston, an igniter, and a driving unit operatively coupled to each other,
    the syringe part coupled to the plunger,
    the plunger coupled to the piston,
    the piston included in the driving unit; and
    providing a button and a power source in the housing, wherein the power source is coupled to the button to provide power to the igniter in response to the button 60 being activated;

accommodating a solution containing the cells and the substance in an accommodation unit disposed between and coupled to the syringe part and the plunger, the accommodation unit comprising:
    a nozzle, and
    an injection port disposed at a tip of the nozzle;
sealing the injection port with a sealing part;
causing, by a driving unit, a pressure in the accommodation unit to reach a maximum pressure in not longer than 2.0 msec from a pressurization start time for the solution by controlling the piston and the plunger to pressurize the solution accommodated in the accommodation unit;
preventing, by a sealing part, the solution from being injected from the accommodation unit to an outside of the syringe assembly via the injection port at least until the pressure in the accommodation unit reaches the maximum pressure; and
providing a cap covering both the sealing part and a front portion of the syringe part that is aligned with the injection port of the nozzle, the cap fixing the sealing part to the front portion of the syringe part such that the sealing part is positioned between, and in contact with, the injection port and an inner surface of the cap.

12. The method according to claim 11, wherein the causing comprises:
    causing the pressure in the accommodation unit to reach the maximum pressure in not shorter than 0.05 msec and not longer than 2 msec from the pressurization start time by controlling the piston and the plunger to pressurize the solution accommodated in the accommodation unit.

13. The method according to claim 11, wherein the causing comprises causing the pressure in the accommodation unit to reach the maximum pressure of 0.10 MPa or more by controlling the piston and the plunger to pressurize the solution accommodated in the accommodation unit.

14. The method according to claim 11, wherein the causing comprises causing the pressure in the accommodation unit to reach the maximum pressure of 0.35 MPa or more by controlling the piston and the plunger to pressurize the solution accommodated in the accommodation unit.

15. The method according to claim 11, wherein the causing comprises causing the pressure in the accommodation unit to reach the maximum pressure of 35 MPa or less by controlling the piston and the plunger to pressurize the solution accommodated in the accommodation unit.

16. The method according to claim 11, wherein the causing comprises causing the pressure in the accommodation unit to reach the maximum pressure of 33 MPa or less by controlling the piston and the plunger to pressurize the solution accommodated in the accommodation unit.

17. The method according to claim 11, wherein the accommodation unit additionally contains a gas.

18. The method according to claim 11, wherein the substance is DNA containing a gene.

* * * * *